United States Patent
Godlewski

(10) Patent No.: US 7,002,014 B2
(45) Date of Patent: Feb. 21, 2006

(54) PROCESS FOR CONTROLLING CRYSTAL STRUCTURE OF RISEDRONATE

(75) Inventor: Jane Ellen Godlewski, Morris, NY (US)

(73) Assignee: The Procter & Gamble Company, Cincinnati, OH (US)

(*) Notice: Subject to any disclaimer, the term of this patent is extended or adjusted under 35 U.S.C. 154(b) by 0 days.

(21) Appl. No.: 10/901,692

(22) Filed: Jul. 29, 2004

(65) Prior Publication Data

US 2005/0026869 A1    Feb. 3, 2005

Related U.S. Application Data

(60) Provisional application No. 60/491,222, filed on Jul. 30, 2003.

(51) Int. Cl.
*C07F 9/38* (2006.01)
*A61K 31/435* (2006.01)

(52) U.S. Cl. ......................................... 546/22; 514/277
(58) Field of Classification Search .................. 546/22; 514/277
See application file for complete search history.

(56) References Cited

U.S. PATENT DOCUMENTS

| 5,583,122 A | 12/1996 | Benedict et al. |
| 5,622,721 A | 4/1997 | Dansereau et al. |
| 6,410,520 B1 | 6/2002 | Cazer et al. |
| 2002/0002282 A1 | 1/2002 | Cazer et al. |

FOREIGN PATENT DOCUMENTS

WO    WO01/56983    *  8/2001

OTHER PUBLICATIONS

Gossman, W.L. et al., "Three Hydrates of the Bisphosphonate Risedronate, Consisting of One Molecular and Two Ionic Structures", *Acta Crystallographica Section C. Crystal Structure Communication*, 2003, pp. M33-M36, vol. 50, No. 2.

Nicbolbon et al., "A General Method of Preparation of Tetramethyl Alkyl-1-hydroy-1, 1-diphosphonates", *J. of Organic Chemistry*, 1971, vol. 36, No. 24, pp. 3844-3845.

Ebetino et al, "Elucidation of Pharmacophore for the Bisphosphonate Mechanism of Bone Antiresorptive Activity", *Phosphorus, Sulfur, and Silicon*, 1996, vols. 109-110, pp. 217-220.

Ebetino et al., "Recent Work on the Synthesis of Phosphonate-Containing, Bone-Active Heterocycles", *Heterocycles*, 1990, vol., 30, No. 2, pp. 855-862.

* cited by examiner

*Primary Examiner*—Rita Desai
(74) *Attorney, Agent, or Firm*—Richard S. Echler, Sr.

(57) ABSTRACT

The present invention relates to a process for controlling the crystal form of 3-pyridyl-1-hydroxy-ethylidene-1,1-bisphosphonic acid salt (Risedronate). The process employs a pH adjustment step to induce the proper hydrate form and thereby avoiding inadvertent nucleation of undesired hydrate forms.

27 Claims, No Drawings

PROCESS FOR CONTROLLING CRYSTAL STRUCTURE OF RISEDRONATE

CROSS REFERENCE TO RELATED APPLICATIONS

This application claims priority under Title 35, United States Code 119(e) from Provisional Application Ser. No. 60/491,222, filed Jul. 30, 2003.

FIELD OF THE INVENTION

The present invention relates to a process for controlling the crystal form of 3-pyridyl-1-hydroxy-ethylidene-1,1-bisphosphonic acid salt (Risedronate). The process employs a pH adjustment step to induce the proper hydrate form and thereby avoiding inadvertent nucleation of undesired hydrate forms.

BACKGROUND OF THE INVENTION

Bisphosphonates such as 3-pyridyl-1-hydroxyethylidene-1,1-bisphosphonic acid (Risedronate) have been proposed for use in the treatment of diseases of bone and calcium metabolism. Such diseases include osteoporosis, hyperparathyroidism, hypercalcemia of malignancy, ostolytic bone metastases, myosistis ossifcans progressive, calcinoisis universalis, arthritis, neuritis, bursitis, tendonitis and other inflammatory conditions. Paget's disease and heterotropic ossification are currently successfully treated with both EHDP (ethane-1-hydroxy-1,1-diphosphonic acid) and Risedronate.

It is known in the literature that some bisphosphonic acids and their salts are capable of forming hydrates, Risedronate sodium exists in three hydration states: mono, hemipenta and anhydrous. Crystallization procedures which selectively yield the hemipentahydrate form over the exclusion of the monohydrate and anhydrous forms are desirable.

SUMMARY OF THE INVENTION

The present invention relates to the surprising discovery that the 3-pyridyl-1-hydroxy-ethylidene-1,1-bisphosphonic acid salt (Risedronate) hydrate form can be selectively controlled in a process which utilizes a pH adjustment step rather than a solvent based nucleation step.

The process of the present invention comprises the steps of:
a) dissolving in an admixture of isopropyl alcohol and water, 3-pyridyl-1-hydroxy-ethylidene-1,1-bisphosphonic acid and an inorganic base in sufficient amount to provide a pH of 6, to form a solution;
b) heating the solution from about 50° C. to about 60° C. to form a heated solution;
c) filtering said heated solution to form a filtered solution;
d) adjusting the pH of said filtered solution with an inorganic acid to a pH range of from 4.7 to 5 while maintaining the temperature at the level obtained in step (b) to form a neutralized solution;
e) cooling the neutralized solution to a temperature of about 20° C. to about 40° C. to form a nucleating slurry of 3-pyridyl-1-hydroxyethylidene-1,1-bisphosphonic acid salt;
f) adding to said slurry isopropyl alcohol and sufficient inorganic acid to provide a pH of from 4.7 to 5.2 to form a ripened slurry of 3-pyridyl-1-hydroxyethylidene-1,1-bisphosphonic acid salt in the hemipentahydrate crystal form; and
g) isolating 3-pyridyl-1-hydroxyethylidene-1,1-bisphosphonic acid salt hemipentahydrate.

It is also an object of the present invention to provide a process for crystallizing Risedronate in the desired crystal form, said process adaptable to inadvertent or accidental formation of undesired monohydrate crystals.

These and other objects, features, and advantages will become apparent to those of ordinary skill in the art from a reading of the following detailed description and the appended claims. All percentages, ratios and proportions herein are by weight, unless otherwise specified. All temperatures are in degrees Celsius (° C.) unless otherwise specified. All documents cited are in relevant part, incorporated herein by reference; the citation of any document is not to be construed as an admission that it is prior art with respect to the present invention.

DETAILED DESCRIPTION OF THE INVENTION

The present invention relates to a process whereby the final crystal form of 3-pyridyl-1-hydroxyethylidene-1,1-bisphosphonic acid salt can be controlled. 3-Pyridyl-1-hydroxy-ethylidene-1,1-bisphosphonic acid salt can exist in several forms, inter alia, hemipentahydrate, monohydrate, and anhydrous. The present invention provides the formulator with a process for preparing a final product which has a single crystalline form.

The present process, by utilizing a pH adjustment step to induce nucleation of the desired crystal form, foregoes the induction by means of solvent addition. This removes the possibility of chemical or thermal shock to the 3-pyridyl-1-hydroxyethylidene-1,1-bisphosphonic acid salt crystallizing system, which can cause the unwanted formation of monohydrate crystals when hemipentahydrate crystals are desirable.

The present invention thereby relates to a process wherein the hemipentahydrate crystal form is produced to the exclusion of the monohydrate form.

Process

The process of the present invention involves several steps, as well as several optional steps which are not required.

Step (a):

Step (a) of the present invention relates to dissolving in an admixture of isopropyl alcohol and water, 3-pyridyl-1-hydroxy-ethylidene-1,1-bisphosphonic acid and adding an inorganic base in a sufficient amount to provide a solution pH of 6, and thereby forming a solution.

The relative amounts of isopropyl alcohol and water can be adjusted by the formulator to insure the success of the subsequent process steps. For example, more or less isopropyl alcohol can be used depending upon the amount of solute (Risedronate) which is to be dissolved and formed into a solution during Step (a). In one embodiment, for each gram of 3-pyridyl-1-hydroxy-ethylidene-1,1-bisphosphonic acid to be crystallized, 8.2 grams of water and 1.23 grams of isopropyl alcohol are combined to form an admixture to which the solute is added. In another embodiment 9.7 grams of water and 1.62 grams of isopropyl alcohol are combined per gram of Risedronate.

Once the 3-pyridyl-1-hydroxy-ethylidene-1,1-bisphosphonic acid has been added to the aqueous isopropyl alcohol admixture, an inorganic base is added in a amount sufficient to provide a solution pH of 6. Non-limiting examples of inorganic bases suitable for use in the process of the present invention include NaOH, NaOCH$_3$, and NaOC(O)CH$_3$. For the purposes of the present invention an "inorganic base" includes "de-protunated organic radicals", inter alia, –OCH$_3$ (methoxide). The base can be added as an aqueous solution, as a solution in isopropyl alcohol/water, or as a solid. The base can be added in one amount, in portions, or continuous depending upon the equipment being used or the relative amounts of isopropyl alcohol and water. In one iteration the ratio of isopropyl alcohol to water in Step (a) is adjusted to a ratio of from 0% to 30%, in another iteration from 0% to 17%.

In one embodiment, 2 equivalents of a 16.7% by weight aqueous solution of NaOH are added to the suspension of Risedronate in isopropyl alcohol/water (1.1 gram isopropyl alcohol to 6.7 grams of water-1:6.6 w/w) with good stirring. In yet another embodiment of the present invention the ratio of isopropyl alcohol to water is 1:5.9, while another embodiment provides a ratio of water to isopropyl alcohol 1:9.1. The solution thus formed in Step (a) is stirred or otherwise agitated until a clear solution is formed. However, the inorganic base can be added in any concentration provided the formulator takes into account the excess water delivered into the process. For example, a 0.1 N solution is as suitable as a 50% w/w solution provided the excess water is accounted for.

Step (b):

Step (b) of the present invention relates to heating the solution to a temperature of from about 50° C. to about 60° C. form a heated solution.

In one embodiment the solution formed in Step (a) is heated to 55° C. until the solution is clear and homogeneous. However, heating to a temperature of 60° C. or higher may not significantly affect the process of the present invention if the heating is not prolonged. Heating higher than 55° C., but lower than 60° C. may be necessary in some iterations of the present process. Another embodiment maintains the solution in a range of from 52° C. to 58° C. Heating to and holding the solution at a temperature of 55° C.±5° C. until Step (e) below is necessary to insure that the Risedronate remains in solution throughout the process.

The amount of time the solution is held at the final temperature is predicated on the rate at which the solution clarifies, which itself may be dependant upon one or more factors, inter alia, the relative composition of the isopropyl alcohol/water solution, and the solute concentration.

Step (c):

Step (c) of the present invention relates to filtering said heated solution to form a filtered solution. In one embodiment the filter is washed with water and the total filtrate maintained at the temperature of Step (b) before transferring to either another vessel or to the original vessel. The rate at which filtration of the heated solution takes place does not impact the process of the present invention unless the temperature of the heated solution is not maintained above about 50° C. More than one filter can be used in series.

The process of the present invention can further comprise an optional Step (c) (i), said step comprising:

c) (i) adding to said filtered solution 3-pyridyl-1-hydroxyethylidene-1,1-bisphosphonic acid salt hemipentahydrate seed crystals.

The seed crystals which are utilized in this optional step can be obtained from a prior isolated and characterized batch or conveniently obtained from the nucleating solution which comprises the product of Step (e).

Step (d):

Step (d) of the present invention relates to adjusting the pH of said filtered solution with an inorganic acid to a pH range of from 4.7 to 5 while maintaining the temperature at the level obtained in Step (b) to form a neutralized solution.

Non-limiting examples of inorganic acids which can be used to adjust the pH range include HCl, H$_2$SO$_4$, and H$_3$PO$_4$. In one embodiment, 12 N HCl (0.35 equivalent per equivalent of inorganic base used in Step (a) herein above) is added at a level below the surface of the stirred solution. Once the desired amount of acid is added the formulator can continue stirring unit the solution is homogeneous or until a stable pH is obtained. In one embodiment, the solution is stirred at the temperature obtained in Step (b) for 30 minutes.

However, if the formulator has adjusted the relative composition of solvent (isopropyl alcohol/water ratio) or the concentration of solute such that neutralization of the solution begins nucleation of the desired hemipentahydrate crystal form, then it may not be necessary to hold and stir the neutralized solution for any significant period of time.

Step (e):

Step (e) of the present invention relates to cooling the neutralized solution to a temperature of about 20° C. to about 30° C. to form a nucleating slurry of 3-pyridyl-1-hydroxyethylidene-1,1-bisphosphonic acid salt. During this step crystals are ripened and the bulk of the crystal recovery is performed.

The neutralized solution obtained from Step (d) may be cooled at any rate which provides for homogeneous formation of the hemipentahydrate. In one embodiment of the present invention, the solution is cooled linearly to a temperature of 25° C. over a period of 2.5 hours during which time the nucleating slurry is stirred to insure formation of the desired crystals. However, the rate at which the solution is cooled can be adjusted by the formulator depending upon the composition of the liquid phase and the concentration of solute in Step (a).

In another embodiment the final temperature in Step (e) is from 20° C. to 40° C., while in yet another embodiment, cooling to a range of from 20° C. to 30° C. is used to ensure a thorough ripening of the desired crystal form.

The present invention makes use of the fact that the saturated nucleation solution can be re-heated or held at a temperature between the temperature of Step (b) and the final desired temperature of Step (e) if unwanted monohydrate crystals are present, thereby providing the following optional Steps (e) (i) and (e) (ii), said steps comprising:

e) (i) holding said nucleating slurry to a temperature from about 20° C. to about 30° C. and holding said slurry at said temperature until said monohydrate form is converted to said hemipentahydrate form;

e) (ii) repeating step (e).

Because these optional steps may be necessary due to unforeseen circumstances which cause the undesirable formation of monohydrate crystals, the formulator may also modify one or more of the conditions of Step (e), inter alia, the rate of cooling or the final temperature.

Step (f):

Step (f) of the present invention relates to adding to said nucleating slurry obtained in Step (e), isopropyl alcohol and sufficient inorganic acid to provide a pH of from 4.7 to 5.2 to form a ripened slurry of 3-pyridyl-1-hydroxyethylidene-1,1-bisphosphonic acid salt in the hemipentahydrate crystal form. The ripened slurry comprises the bulk of the Risedronate which was charged to the process in Step (a).

The isopropyl alcohol is added to the nucleating slurry prior to adjusting the pH to the desired range. In one embodiment, isopropyl alcohol in an amount 0.25 times the weight of water present is added with full agitation followed by stirring for 30 minutes.

Non-limiting examples of inorganic acids which can be used to adjust the pH range once the final aliquot of isopropyl alcohol is added, include HCl, $H_2SO_4$, and $H_3PO_4$. Once the desired amount of acid is added the formulator can continue stirring unit crystallization is complete.

In the event the pH range of the final nucleating slurry is lower than the desired final range, an inorganic base can be used to adjust the pH to the desired range. Suitable inorganic bases include those described herein above for Step (a).

There are several iterations by which Step (f) can be conducted. For Example, in a first iteration the isopropyl alcohol and inorganic acid used to form said ripened slurry is added as an admixture. This admixture can be added above or below the level of liquid in the nucleating slurry. Alternatively, the isopropyl alcohol can be added separately from said and inorganic acid either completely or in an alternating manner.

Step (g):

Step (g) of the present invention relates to isolating 3-pyridyl-1-hydroxyethylidene-1,1-bisphosphonic acid salt hemipentahydrate. This step can be accomplished in any manner which is compatible with the equipment used in the steps herein above.

One means for isolating the Risedronate crystals is by filtration, either via gravity or via vacuum. However, the formulator may instead desire to decant the filtrate to provide the final product.

The process of the present invention relates to controlling nucleation and crystal form by adjusting the pH of the solute saturated solution and, therefore, addition of isopropyl alcohol must be done in a manner which does not shock the stabilized system and cause the undesired formation of monohydrate crystals. In addition, controlled cooling below the temperature utilized in Step (b) will ensure controlled growth of the desired hemipentahydrate crystals.

One embodiment of the present invention comprises the steps of:
 a) dissolving in an admixture of isopropyl alcohol and water, 3-pyridyl-1-hydroxy-ethylidene-1,1-bisphosphonic acid and NaOH in sufficient amount to provide a pH of 6, to form a solution;
 b) heating the solution to 55° C. to form a heated solution;
 c) filtering said heated solution to form a filtered solution, while maintaining a temperature of 55° C.;
 d) adjusting the pH of said filtered solution with HCl to a pH range of from 4.7 to 5, while maintaining a temperature of 55° C., to form a neutralized solution;
 e) cooling the neutralized solution to 25° C. to form nucleating slurry of 3-pyridyl-1-hydroxyethylidene-1,1-bisphosphonic acid salt; and
 f) adding to said slurry isopropyl alcohol and sufficient HCl to provide a pH of from 4.7 to 5.2 to form a ripened slurry of 3-pyridyl-1-hydroxyethylidene-1,1-bisphosphonic acid salt in the hemipentahydrate crystal form The following is a non-limiting example of the process of the present invention.

a) To a first vessel is charged water (1640 mL) and isopropyl alcohol (246 g). The solution is stirred and 3-pyridyl-1-hydroxy-ethylidene-1,1-bisphosphonic acid (Risedronate) (200 g) is added. With stirring, a 16.7% aqueous solution of NaOH (318.1 g, 2.0 eq, 1.328 mol) is added.

b) The solution is then heated to 55° C. and held at a temperature of 55±5° C. until all of the solute has dissolved.

c) The solution is then filtered and transferred to a second vessel which is pre-heated to a temperature of 55±5° C. The filter is washed with water (80 g).

d) While maintaining the temperature at about 55° C., 12 N HCl (38.7 mL, 0.7 eq., 0.465 mol) is added to provide a pH of from 4.7 to 5.0. The solution is stirred for 30 minutes.

e) The solution is then slowly cooled to 25° C. over a period of 2.5 hours and a nucleating slurry of Risedronate forms.

f) Isopropyl alcohol (410 g) is added to the nucleating slurry and the contents stirred for 30 minutes after which sufficient HCl is added to provide a pH of from 4.7 to 5.2.

g) After stirring for an additional hour the crystals of Risedronate which have formed are collected by filtration.

A further embodiment of the present invention relates to a process wherein lower yields with higher purity are obtained, said embodiment comprising the steps of:
 a) dissolving in an admixture of isopropyl alcohol and water, 3-pyridyl-1-hydroxy-ethylidene-1,1-bisphosphonic acid and an inorganic base in sufficient amount to provide a pH of 6, to form a solution;
 b) heating the solution from about 50° C. to about 60° C. to form a heated solution;
 c) filtering said heated solution to form a filtered solution;
 d) adjusting the pH of said filtered solution with an inorganic acid to a pH range of from 4.7 to 5 while maintaining the temperature at the level obtained in step (b) to form a neutralized solution;
 e) cooling the neutralized solution to a temperature of about 20° C. to about 40° C. to form a nucleating slurry of 3-pyridyl-1-hydroxyethylidene-1,1-bisphosphonic acid salt; and
 f) isolating 3-pyridyl-1-hydroxyethylidene-1,1-bisphosphonic acid salt hemipentahydrate.

All documents cited in the Detailed Description of the Invention are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A process for preparing 3-pyridyl-1-hydroxyethylidene-1,1-bisphosphonic acid salt in the hemipentahydrate crystal form, said process comprising the steps of:
 a) dissolving in an admixture of isopropyl alcohol and water, 3-pyridyl-1-hydroxyethylidene-1, 1-bisphosphonic acid and an inorganic base in sufficient amount to provide a pH of 6, to form a solution;
 b) heating the solution from about 50° C. to about 60° C. to form a heated solution;
 c) filtering said heated solution to form a filtered solution;
 d) adjusting the pH of said filtered solution with an inorganic acid to a pH range of from 4.7 to 5 while maintaining the temperature at the level obtained in step (b) to form a neutralized solution;

e) cooling the neutralized solution to a temperature of about 20° C. to about 40° C. to form a nucleating slurry of 3-pyridyl-1-hydroxyethylidene-1,1-bisphosphonic acid salt;

f) adding to said slurry isopropyl alcohol and sufficient inorganic acid to provide a pH of from 4.7 to 5.2 to form a ripened slurry of 3-pyridyl-1-hydroxyethylidene-1,1-bisphosphonic acid salt in the hemipentahydrate crystal form; and g) isolating 3-pyridyl-1-hydroxyethylidene-1,1-bisphosphonic acid salt hemipentahydrate.

2. A process according to claim 1 wherein the ratio of isopropyl alcohol to water in step (a) is 1:6.7.

3. A process according to claim 1 wherein rhc ratio of isopropyl alcohol to water in step (a) is from 1:5.9 to 1:9.1.

4. A process according to claim 1 wherein said inorganic base is step (a) is selected from the group consisting of NaOH, NaOCH$_3$, and NaOC(O)CH$_3$.

5. A process according to claim 4 wherein said inorganic base is NaOH.

6. A process according to claim 1 wherein said temperature in step (b) is from 52° C. to 58° C.

7. A process according to claim 6 wherein said temperature is 55° C.

8. A process according to claim 1 wherein said filtered solution formed in step (c) has the same temperature as the heated solution formed in step (b).

9. A process according to claim 1 wherein said inorganic acid in step (d) is selected from the group consisting of HCl, H$_2$SO$_4$, and H$_3$PO$_4$.

10. A process according to claim 9 wherein said inorganic acid is HCl.

11. A process according to claim 1 wherein said temperature in step (e) is from 20° C. to 40° C.

12. A process according to claim 11 wherein said temperature is from 20° C. to 30° C.

13. A process according to claim 12 wherein said temperature is 25° C.

14. A process according to claim 1 wherein said inorganic acid in step (f) is selected from the group consisting of HCl, H$_2$SO$_4$, and H$_3$PO$_4$.

15. A process according to claim 14 wherein said inorganic acid is HCl.

16. A process according to claim 1 wherein said isopropyl alcohol and inorganic acid used to form said ripened slurry in step (f) is added as an admixture.

17. A process according to claim 1 wherein said isopropyl alcohol added in step (f) is added separately from said and inorganic acid.

18. A process according to claim 17 wherein said isopropyl alcohol and said inorganic acid are added separately but concurrently.

19. A process according to claim 17 wherein said isopropyl alcohol and said inorganic arid are added in alternating portions.

20. A process according to claim 1 wherein said product isolated in step (g) is isolated by filtration.

21. A process according to claim 1 wherein said product isolated in step (g) is isolated by decanting the solvent.

22. A process according to claim 1 wherein said product isolated in step (g) is isolated by centrifugation.

23. A process according to claim 1 having the optional step (c) (i), said step comprising:

c) (i) adding to said filtered solution 3-pyridyl-1-hydroxyethylidene-1,1-bisphosphonic acid salt hemipentahydrate seed crystals.

24. A process according to claim 1 wherein said product formed in step (f) is in the platelet crystal form.

25. A process according to claim 1 wherein when said nucleating slurry formed in step (e) comprises an admixture of monahydrate and hemipentahydrate crystal forms, said process having further c) (i) holding said nucleating slurry to a temperature from about 20° C. to about 30°C. and holding said slurry at said temperature until said monohydrate form is converted to said hemipentahydrate form;

e) (ii) repeating step (e).

26. A process for preparing 3-pyridyl-1-hydroxyethylidene-1,1-bisphosphonic acid salt in the hemipentahydrate crystal form, said process comprising the steps of:

a) dissolving in an admixture of isopropyl alcohol and water, 3-pyridyl-1-hydroxyethylidene-1,1-bisphosphonic acid and an inorganic base in sufficient amount to provide a pH of 6, to form a solution;

b) heating the solution from about 50° C. to about 60° C. to form a heated solution;

c) filtering said heated solution to form a filtered solution;

d) adjusting the pH of said filtered solution with an inorganic acid to a pH range of from 4.7 to 5 while maintaining the temperature at the level obtained in step (b) to form a neutralized solution;

e) cooling the neutralized solution to a temperature of about 20° C. to about 40° C. to form a nucleating slurry of 3-pyridyl-1-hydroxyethylidene-1,1-bisphosphonic acid salt; and f) isolating 3-pyridyl-1-hydroxyethylidene-1,1-bisphosphonic acid salt hemipentahydrate.

27. A process for preparing 3-pyridyl-1-hydroxyethylidene-1,1-bisphosphonic acid salt in the hemipentahydrate crystal form, said process comprising the steps of:

a) dissolving in an admixture of isopropyl alcohol and water, 3-pyridyl-1-hydroxyethylidene-1,1-bisphosphonic acid arid NaOH in sufficient amount to provide a pH of 6, to form a solution;

b) heating the solution to 55° C. to form a heated solution;

c) filtering said heated solution to form a filtered solution, while maintaining a temperature of 55° C.;

d) adjusting the pH of said filtered solution with HCl to a pH range of from 4.7 to 5, while maintaining a temperature of 55° C., to form a neutralized solution;

e) cooling the neutralized solution to 25° C. to form nucleating slurry of 3-pyridyl-1-hydroxyethylidene-1,1-bisphosphonic acid salt; and f) adding to said slurry isopropyl alcohol and sufficient HCl to provide a pH of from 4.7 to 5.2 to form a ripened slurry of 3-pyridyl-1-hydroxyethylidene-1,1-bisphosphonic acid salt in the hemipentahydrate crystal form.

* * * * *

UNITED STATES PATENT AND TRADEMARK OFFICE
CERTIFICATE OF CORRECTION

| | |
|---|---|
| PATENT NO. | : 7,002,014 B2 |
| APPLICATION NO. | : 10/901692 |
| DATED | : February 21, 2006 |
| INVENTOR(S) | : Jane Ellen Godlewski |

Page 1 of 1

It is certified that error appears in the above-identified patent and that said Letters Patent is hereby corrected as shown below:

Column 7
       Line 16, please delete "rhc" and insert -- the --.
       Line 56, please delete "arid" and insert --acid --.

Column 8
       Line 45, please delete "arid" and insert -- and --.

Signed and Sealed this

Fifth Day of August, 2008

JON W. DUDAS
*Director of the United States Patent and Trademark Office*